US006465696B1

(12) United States Patent
Zhou et al.

(10) Patent No.: US 6,465,696 B1
(45) Date of Patent: Oct. 15, 2002

(54) INTEGRATED PROCESS FOR SYNTHESIZING ALCOHOLS, ETHERS, AND OLEFINS FROM ALKANES

(75) Inventors: Xiao Ping Zhou; Galen D. Stucky, both of Goleta, CA (US); Jeffrey H. Sherman, The Woodlands, TX (US)

(73) Assignees: GRT, Inc., The Woodlands, TX (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/951,739

(22) Filed: Sep. 11, 2001

Related U.S. Application Data (63) Continuation-in-part of application No. 09/886,078, filed on Jun. 20, 2001.

(51) Int. Cl.[7] .................... C07C 27/00; C07C 41/00; C07C 27/10; C07C 69/02; C07C 67/10
(52) U.S. Cl. .................. 568/671; 568/891; 568/893; 568/910; 560/231; 560/236
(58) Field of Search ................. 568/671, 891, 568/893, 910; 560/231, 236

(56) References Cited

U.S. PATENT DOCUMENTS

| | | | |
|---|---|---|---|
| 3,172,915 A | 3/1965 | Borkowski et al. | 260/614 |
| 3,310,380 A | 3/1967 | Lester | 23/216 |
| 5,243,098 A | 9/1993 | Miller et al. | 568/893 |
| 5,334,777 A | 8/1994 | Miller et al. | 568/859 |
| 5,998,679 A | 12/1999 | Miller | 568/859 |

FOREIGN PATENT DOCUMENTS

| | | |
|---|---|---|
| WO | PCT/IE99/05576 | 7/1999 |

OTHER PUBLICATIONS

Selective Monohalogenation of Methane over Supported Acid or Platinum Metal Catalysts and Hydrolysis of Methyl Halides over y–Alumina–Supported Metal Oxide/Hydroxide Catalysts. A Feasible Path for the Oxidative Conversion of Methane into Methyl Alcohol/Dimethyl Ether; George B. Olah, et al.; Contribution from the Donald P. and Katherine B. Loker Hydrocarbon Research Institute and Department of Chemistry, University of Southern California, Los Angeles, CA; received Apr. 22, 1985.

*Primary Examiner*—Samuel Barts
*Assistant Examiner*—Elvis O. Price
(74) *Attorney, Agent, or Firm*—Michael A. O'Neil (57) ABSTRACT

Alcohols, ethers, and olefins are manufactured from alkanes by mixing an alkane and bromine in a reactor to form alkyl bromide and hydrogen bromide. The alkyl bromide only or the alkyl bromide and the hydrogen bromide are directed into contact with metal oxide to form an alcohol and/or an ether, or an olefin and metal bromide. The metal bromide is oxidized to form original metal oxide and bromine, both of which are recycled.

18 Claims, 3 Drawing Sheets

INTEGRATED PROCESS FOR SYNTHESIZING ALCOHOLS, ETHERS, AND OLEFINS FROM ALKANES

CROSS REFERENCE TO RELATED APPLICATION

This is a continuation-in-part application under 37 C.F.R. §1.63 of application Ser. No. 09/886,078 filed Jun. 20, 2001, currently pending.

TECHNICAL FIELD

This invention relates generally to the synthesis of alcohols, ethers, and olefins from alkanes, and more particularly to a method of and apparatus for manufacturing methanol and dimethyl ether from methane; for manufacturing ethanol, diethyl ether, and ethyl acetate from ethane; and for converting alkanes, which have more than two carbon atoms in their molecular structure, to their corresponding olefins.

BACKGROUND OF THE INVENTION

Methane has previously been converted to methanol by the halogenation of methane followed by hydrolysis of the methyl halide to form methanol. For example, gaseous chlorine has been used to chlorinate methane to form chlorinated methane, principally methyl chloride, together with other chlorides, i.e., dichloromethane, trichloromethane and carbon tetrachloride. Alternatively, methane has been subjected to oxychlorination with oxygen and hydrochloric acid to form the foregoing compounds. The chlorinated methanes produced are hydrolyzed in the vapor phase to produce methanol, formaldehyde, formic acid and by-products, including carbon dioxide and hydrochloric acid, depending on the chlorination selectivity. Hydrochloric acid is produced or used in the halogenation of methane by either method and must be recovered, dehydrated by azeotropic distillation and recycled. Corrosion and other problems involved with the handling of chlorine and hydrochloric acid are substantial.

U.S. Pat. No. 3,172,915 granted to Borkowski, et al. is directed to a process for converting methane to methanol. Borkowski discloses the chlorination of methane using ferric chloride at high temperatures to produce chloromethanes and hydrogen chloride. The process requires temperatures in the range of 220–800° C., more preferably 250–450° C., and long residence times, e.g., more than one hour. Further, the process is hindered by the production of a mixture of chlorination products, e.g., chloromethane, dichloromethane, trichloromethane and carbon tetrachloride, which must be separated before hydrolysis to methanol. Other disadvantages result from the energy required to dry the ferric chloride and from the corrosion and handling problems inherent with hydrochloric acid.

U.S. Pat. No. 5,243,098 granted to Miller discloses another method for converting methane to methanol. In the Miller process the reaction of methane with cupric chloride produces chloromethane and hydrochloric acid. These intermediates are then reacted with steam and a catalyst containing magnesium oxide to produce methanol and magnesium chloride. Magnesium oxide is regenerated by treatment of the magnesium chloride by-product with air or oxygen. Cupric chloride is regenerated by treatment of the cuprous chloride by-product with air and hydrochloric acid. Although these reactions proceed at favorable rates, attrition of the solid reactants, i.e., cupric and magnesium oxide, is significant. Special filters and processes are required to recover and regenerate the reactants in the required particle size. Miller also suggests cupric bromide and magnesium zeolite as alternative reactants. Because of the attrition of the reactants, difficulties associated with the handling of solids, and the special filters and processes required to regenerate the reactants, the Miller process has proved unsatisfactory. U.S. Pat. No. 5,334,777, also granted to Miller, discloses a nearly identical process for converting ethane to ethylene glycol.

U.S. Pat. No. 5,998,679 granted to Jorge Miller, discloses a process for converting alkanes and alkenes to the corresponding lower alkanols and diols. In the method of the invention, a gaseous halogen (bromine) is produced by decomposing a metal halide in a liquid having a melting point below and a boiling point above the decomposition temperature of the metal halide. The preferred liquid is molten hydrated ferric chloride maintained at a temperature between about 37–280° C. The lower alkane or alkene is halogenated in a gas phase reaction with the halogen. The resulting alkyl halide or alkyl dihalide is contacted with a metal hydroxide, preferably an aqueous solution of ferric hydroxide, to regenerate the metal halide and produce the corresponding lower alkanol or diol. Problems with this process include low monohalogenation selectivity, and corrosiveness of the hydrated ferric halides, which may present a containment problem if the process is run at 280° C., where high pressure steam is required to maintain ferric halide hydration. Finally, the process produces a great deal of water and HCl or HBr, all of which are difficult to separate on a large scale from the desired product methanol.

Published international patent application WO 00/07718, naming Giuseppe Bellussi, Carlo Perego, and Laura Zanibelli as inventors, discloses a method for directly converting methane and oxygen to methanol over a metal halide/metal oxide catalyst. This is not a catalyst in the true sense, however, because the reaction involves transfer of halide from a metal halide via reaction with methane to a different metal oxide producing the metal halide and methanol downstream. Eventually the halide is leached and the catalyst loses activity.

Olah et al. (George A. Olah, et al. *J. Am. Chem. Soc.* 1985, 107, 7097–7105) discloses a method for converting methane to methanol via methyl halides ($CH_3Br$ and $CH_3Cl$), which are then hydrolyzed to prepare methanol. In the process, $CH_3Br$ and $CH_3Cl$ are hydrolyzed over catalysts with excess steam generating a methanol, water, and a HCl or HBr mixture. The separation of methanol (about 2% by mole) from HCl or HBr and water on an industry scale (2000 tons per day) requires an enormous amount of energy and generates a great deal of aqueous HCl or HBr waste. Aqueous HCl and HBr are very corrosive as well.

SUMMARY OF THE INVENTION

The present invention comprises a process wherein bromine or a bromine-containing compound is used as an intermediate to convert alkanes to alcohols, ethers, or olefins by reaction with oxygen (or air). While the process can be used to convert a variety of alkanes, including methane, ethane, propane, butane, isobutane, pentanes, hexanes, cyclohexane etc. to their respective alcohols, ethers, or olefins, the conversion of methane to methanol and dimethyl ether is illustrative.

Methane reacts with bromine over a catalyst to form $CH_3Br$ and HBr. $CH_3Br$ and HBr react with a metal oxide to form a variable mixture of dimethyl ether (DME), water and methanol, and the metal bromide. The metal oxide and molecular bromine are regenerated by reaction of the metal bromide with air and/or oxygen. The regenerated bromine is recycled to react with methane while the regenerated metal oxide is used to convert more methyl bromide and HBr to methanol and DME, completing the reaction cycle.

The process can be easily carried out in a riser reactor. Compared to the current industrial two step process, in which methane and steam are first converted to CO and $H_2$ at 8002° C. followed by conversion to methanol over a Zn—Cu—Al—O catalyst at approximately 70—150 atmospheres, the process of the present invention operates at roughly atmospheric pressure and relatively low temperatures, thereby providing a safe and efficient process for methanol production.

The present invention operates with solid/gas mixtures at atmospheric pressure. In the process, the hydrogen halide is gaseous, and therefore not as corrosive as when aqueous at high temperatures. The reaction of $Br_2$ with an alkane can reach more than 90% selectivity and high conversion to alkane-monobromide. The main side products, alkane dibromides such as $CH_2Br_2$, can be converted back to the monobromides by reaction with an alkane over another catalyst. Very few by-products are produced.

During operation, most of the Br atoms are trapped in the solid state, making the system less corrosive. Another advantage is that in the process, DME and alcohol ($CH_3OH$) are not produced as a mixture with excess water. By controlling reaction conditions, almost pure DME and/or methanol is obtained directly so that it is not necessary to separate $CH_3OH$ from water. Finally, in the present process, methane and oxygen do not come into direct contact, resulting in improved safety.

BRIEF DESCRIPTION OF THE DRAWINGS

A more complete understanding of the present invention may be had by reference to the following Detailed Description when taken in connection with the accompanying Drawings, wherein.

DETAILED DESCRIPTION

Alkanes (methane, ethane, propane, butane, isobutane, pentanes, hexanes, cyclohexane etc.) react with molecular bromine over a catalyst composed of all possible metal compounds and mixtures thereof to form alkylbromides. For $CH_4$ (although the process may be applied to higher alkanes as well), the process of the present invention can convert more than 50% $CH_4$ to $CH_3Br$ and HBr, with selectivity higher than 90%. Most of the by-product is $CH_2Br_2$ plus trace amounts of $CHBr_3$ and $CBr_4$, which can be catalytically reconverted to $CH_3Br$ by reacting $CH_2Br_2$, $CHBr_3$, and $CBr_4$ with $CH_4$.

Figure 1:
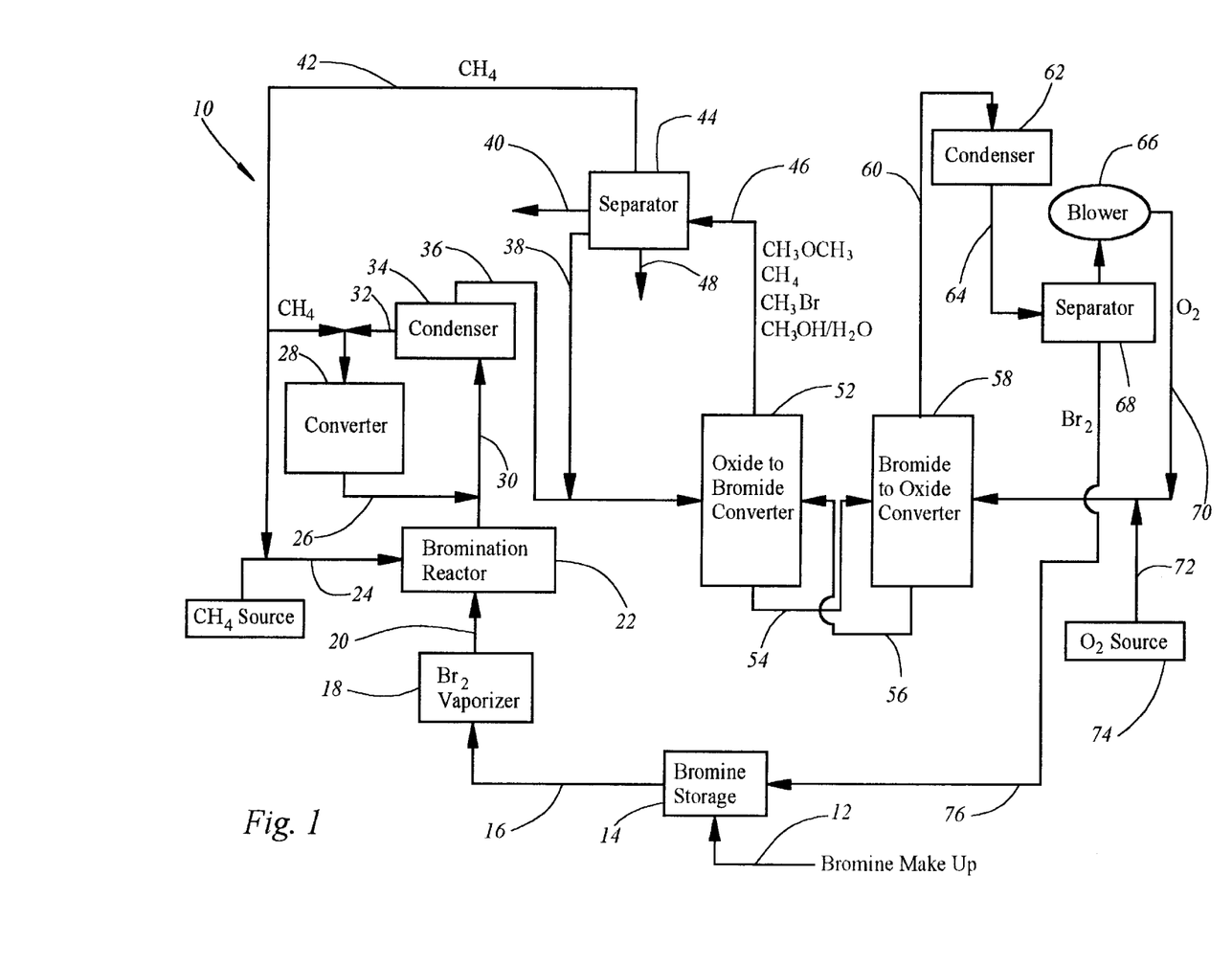
FIG. 1 is a schematic illustration of a method of and apparatus for synthesizing alcohols and/or ethers from alkanes comprising a first version of the first embodiment of the invention.

Referring to the Drawings, and particularly to FIG. 1, a method and apparatus 10 for synthesizing alcohols and ethers from alkanes using bromine comprising a first version of the first embodiment of the invention is schematically illustrated. In the operation of the method and apparatus 10, bromine is received from a suitable source through a line 12 and is directed to a bromine storage container 14. For example, bromine is easily manufactured from bromide, which is readily available from sea water.

As is well known, bromine is a liquid at room temperature. Liquid bromine from the storage container 14 is directed through a line 16 to a bromine vaporizer 18 wherein the bromine is converted from the liquid phase to the gas phase. From the vaporizer 18 the gaseous bromine is directed through a line 20 to a reactor 22.

Methane from a suitable source is directed to the reactor 22 through a line 24. Within the reactor 22 the methane and the gaseous. bromine are mixed together over an appropriate solid catalyst, and the temperature of the mixture is raised to between about 20° C. and about 600° C., thereby converting the methane and the bromine to methyl bromide ($CH_3Br$) and hydrogen bromide (HBr).

From the reactor 22 the $CH_3Br$, the HBr, any unreacted methane and byproducts $CH_2Br_2$, $CHBr_3$, and $CBr_4$ are directed to a condenser 34 through a line 30. The byproducts $CH_2Br_2$, $CHBr_3$, and $CBr_4$ are in the liquid state and are sent through a line 32 to a converter 28 to react with methane. In the converter 28 methane reacts with the by products $CH_2Br_2$, $CHBr_3$, and $CBr_4$ to form $CH_3Br$. The newly formed $CH_3Br$ and unreacted $CH_2Br_2$, $CHBr_3$, $CBr_4$ and methane are sent to the condenser 34 through a line 26 and the line 30.

From the condenser 34 gas phase methane, HBr, and $CH_3Br$ are sent to a converter 52 through a line 36. In the converter 52 HBr and $CH_3Br$ react with metal oxide to form $CH_3OCH_3$, $CH_3OH$, and $H_2O$, which are sent to a separator 44 along with unreacted methane and $CH_3Br$ through a line 46.

In the separator 44 dimethyl ether and methanol/water are separated as products and recovered at outlets 40 and 48, respectively. The methanol is subsequently removed from the water by distillation. $CH_3Br$ is sent back to the converter 52 through the line 38 and the line 36. Methane from the separator 44 is sent back to the bromination reactor 22 through the line 42 and the line 24.

In the converter 52, the original metal oxide is converted to metal bromide and must be regenerated. The metal bromide from the converter 52 is sent to a converter 58 through a line 54 to react with oxygen received from a source 74 through a line 72 to regenerate bromine and metal oxide. The regenerated metal oxide is sent back to the converter 52 through a line 56, while the bromine and unreacted oxygen are sent to a condenser 62 through a line 60, after which they are separated in a separator 68. The liquid bromine is sent to the storage container 14, while the oxygen is sent to the converter 58 through a blower 66 and a line 70.

Figure 2:
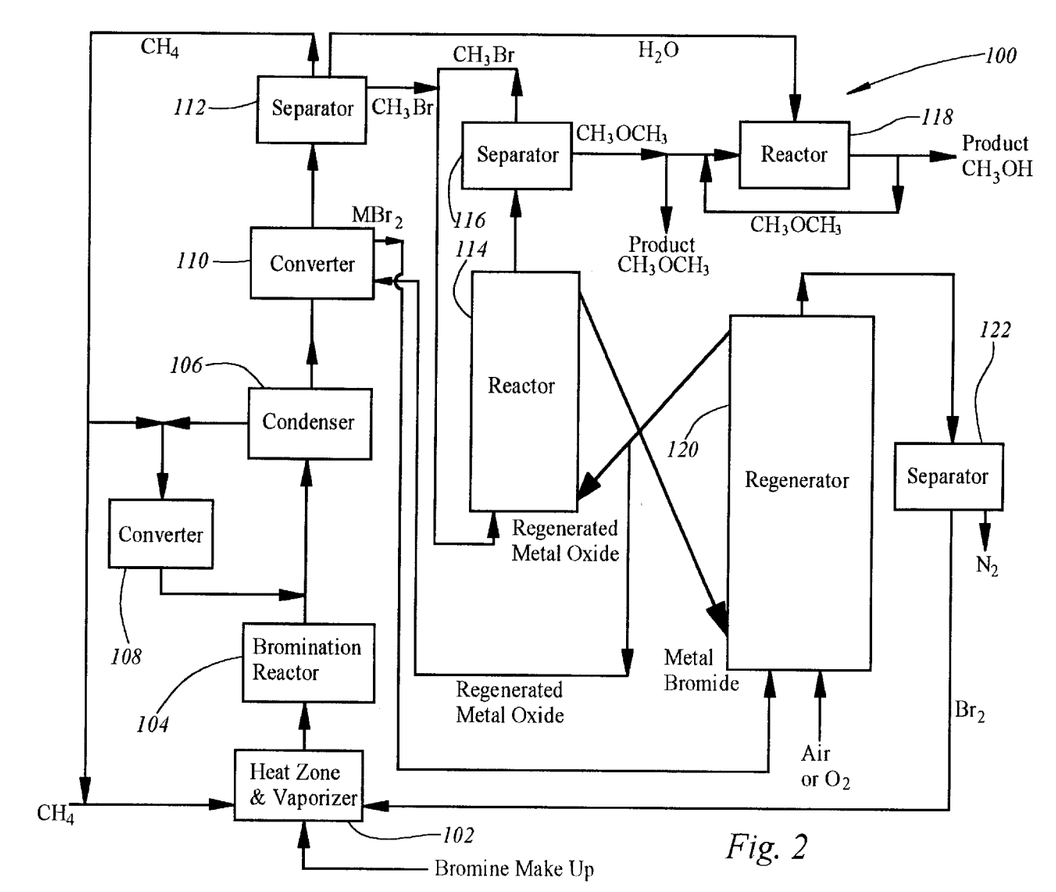
FIG. 2 is a schematic illustration of a method of and apparatus for synthesizing alcohols and/or ethers from alkanes comprising a second version of the first embodiment of the invention.

Referring to FIG. 2, there is shown a method of and apparatus 100 for synthesizing alcohols and ethers from alkanes comprising a second version of the first embodiment of the invention. Methane and bromine are directed to a heat zone and vaporizer 102 where the bromine is converted from a liquid to a gas and mixed with methane at a temperature above the atmospheric boiling point of bromine. The gas mixture is passed into a bromination reactor 104 containing an appropriate solid catalyst. After the reaction, the mixture is directed to condenser a 106. The liquid phase contains by products $CH_2Br_2$, $CHBr_3$, and $CBr_4$, while the gas phase contains bromomethane, HBr, and unreacted methane.

The by products $CH_2Br_2$, $CHBr_3$, and $CBr_4$ are sent to a converter 108 where they react with methane to form bromomethane. After the reaction the mixture is sent to the condenser 106.

The gas phase mixture from the condenser 106 is passed through a converter 110, where HBr reacts with the metal oxide to form metal bromide and water. The metal bromide is sent to a regenerator 120 to regenerate metal oxide. From the converter 110, the water, bromomethane, and methane are separated in a separator 112. Methane is recycled to the converter 108 and the vaporizer 102. Bromomethane is sent to the reactor 114. Water is sent to the reactor 118.

In the reactor 114 bromomethane reacts with metal oxide to generate dimethyl ether(DME) and metal bromide. Metal bromide is sent to the regenerator 120. The mixture of bromomethane and DME from the reactor 114 is sent to a separator 116. Bromomethane is recycled to the reactor 114, while DME is obtained as a product or directed to reactor 118. In the reactor 118 DME reacts with water (from the separator 112) over a catalyst to form methanol.

In the regenerator 120 metal bromide from the converter 110 and the reactor 114 reacts with air or oxygen to regenerate metal oxide and bromine. After regeneration the metal oxide is sent to the converter 110 and the reactor 114, while bromine is sent to the vaporizer 102. If air is used to provide the oxygen for metal oxide, regeneration nitrogen may be purged from the system through the separator 122.

Figure 3:
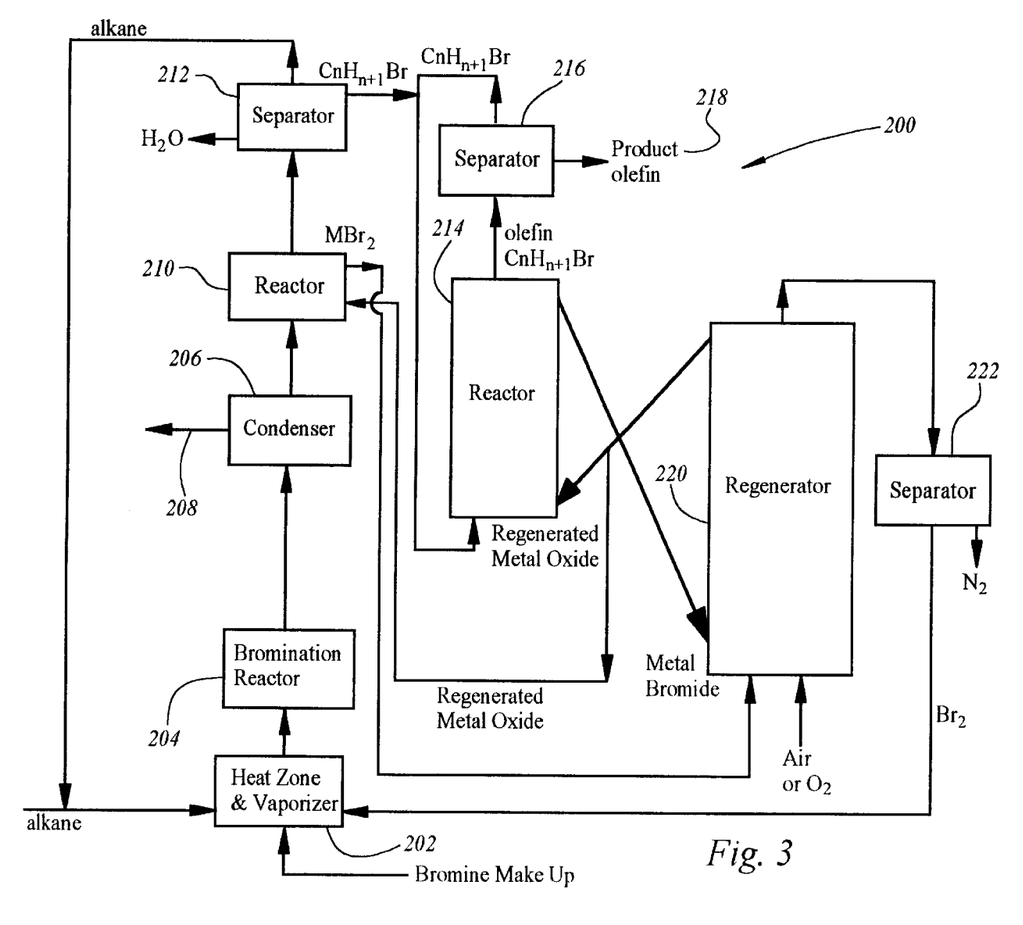
FIG. 3 is a schematic illustration of a method of and apparatus for synthesizing olefins from alkanes comprising a second embodiment of the invention.

Referring to FIG. 3, there is shown a method of and apparatus 200 for synthesizing olefins from alkanes, which have more than two carbon atoms in their molecular structure, comprising a second embodiment of the invention. The alkane and bromine are directed to a heat zone and vaporizer 202, operating at a temperature above the atmospheric boiling point of bromine, where the now gaseous bromine and methane are allowed to mix. The gas mixture is passed into a bromination reactor 204, which contains an appropriate solid catalyst. After the reaction the mixture is directed to a condenser 206. The heavier alkane multibromides (below 1%) are separated for other uses, such as solvent or intermediates for other organic synthesis at an outlet 208, while the alkane monobromide, HBr, and unreacted alkane are sent to a reactor 210.

In the reactor 210 HBr reacts with metal oxide to form metal bromide and water. The metal bromide is sent to a regenerator 220 to be regenerated back to metal oxide. From the reactor 210 the water, alkane monobromide, and alkane are separated in a separator 212. Unreacted alkane is recycled to a vaporizer 202, while the alkane monobromide is sent to a reactor 214. Water is easily separated from the alkane monobromide in the separator 212 as a by product.

In the reactor 214 alkane monobromide reacts with metal oxide to generate olefin and metal bromide. Metal bromide is sent to the regenerator 220 for regeneration back to metal oxide. The mixture of olefin and unreacted alkane monobromide from the reactor 214 is sent to a separator 216 where they are easily separated due to their widely different boiling points. Unreacted alkane monobromide, if any, is recycled to the reactor 214, while olefin is obtained as a product.

In the regenerator 220 metal bromide from the reactor 210 and the reactor 214 reacts with air or oxygen to regenerate metal oxide and bromine. After regeneration metal oxide is sent to the reactor 210 and the reactor 214, while bromine is sent to the vaporizer 202. If air is used as the source of oxygen for regeneration of the metal oxide, nitrogen may be purged from the system by a separator 222.

EXAMPLES

Reaction 1
Catalyst Preparation

$Nb_2O_5$ (0.8000 g) was mixed with 0.500 ml 96(w) % $H_2SO_4$, then the mixture was heated at 110° C. for 4 hours. The temperature increased to 500° C. within 6 hours, and kept at 500° C. for 4 hours. Catalyst C1 was obtained.

$ZrO_2$ (2.0000 g) was mixed with $H_2SO_4$ (3.000 ml, 96(w) %), then the mixture was heated at 110° C. for 4 hours. The temperature increased to 500° C. within 6 hours, and kept at 500° C. for 4 hours. Catalyst C2 was obtained.

Testing
Reaction Conditions

The catalyst was tested at a methane flow of 1.5 ml/minute and $Br_2$ flow of 0.07 ml/hour. The reaction temperature was 400° C. The reaction was carried out in a microreactor system. After 6 hours on line reaction, the reaction effluent was analyzed by a GC/MS. A methane conversion of 24% (mol) with 95% $CH_3Br$ was obtained.

Summarizing the overall process in Reaction 1:

(1)

Reaction 2

Example 1

Reaction on M1

For all of the examples provided above the second stage of the process occurs as follows. After separation of the $CH_2Br_2$, $CHBr_3$ and $CBr_4$ products from the gas stream, the $CH_3Br$, together with the HBr are passed into the next reactor, which contains M1 (50% CuO on $ZrO_2$) and is maintained at 225° C. Flowing the reactant gases at 10 h$^{-1}$ gives a 96% conversion of $CH_3Br$+HBr to $CH_3OCH_3$ and $H_2O$, or to $CH_3OH$, or a mixture of $CH_3OH$, $CH_3OCH_3$, and $H_2O$, with 94% selectivity, the remaining product being $CuBr_2/ZrO_2$ and 6% $CO_2$. Dimethyl ether and water are converted into methanol if desired in a third reactor containing catalysts.

Example 2

Zr Solution Preparation $Zr(OCH_2CH_2CH_3)_4$ (70(w) % in isopropanol, 112.6 ml) was dissolved into acetic acid (275 ml) under stirring. After stirring for 10 minutes, the solution was diluted by water to make a total volume of 500 ml. A solution with a Zr concentration of 0.5M was obtained.

Preparation of M2

$Cu(NO_3)_2$ (0.5M, 7.200 ml) solution was added into $BaBr_2$ (0.5M, 0.800 ml). A clear solution was obtained. To this solution, Zr solution (0.5M) as prepared above was added under stirring. After stirring a few seconds, a gel was obtained. The gel was dried at 110° C. for 4 hours, then heated to 500° C. within 6 hours, and kept at 500° C. for 4 hours. M2 was obtained.

The metal oxide mixture was tested at a $CH_3Br$ flow rate of 1.0 ml/minute at 230° C. In the first half hour, the average $CH_3Br$ conversion was 65%, and the average dimethyl ether selectivity was 90.5%.

Preparation of M3

$Cu(NO_3)_2$ (0.5M, 40.000 ml) solution was added into Zr solution (0.5M, 30.000 ml as prepared above). After stirring a few seconds, a gel was obtained. The gel was dried at 110° C. for 4 hours, then heated to 500° within 6 hours, and calcined at 500° C. for 4 hours. M3 was obtained.

Testing

The catalyst C2 (2.0000 g) was loaded into a first reactor (R1). A trap was loaded with 2.0000 g of $M_3$. A second reactor (R2) was loaded with M3 (0.8500 g).

Reactants methane and bromine were fed into the first reactor (methane flow of 1.5 ml/minute, $Br_2$ flow of 0.07 ml/hour). The reaction temperature was 390° C. After reaction in R1 (stabilized by online reaction for more than 8 hours), the resulting mixture was passed through the trap and a mixture of methane and $CH_3Br$ (containing 20% mol of $CH_3Br$) was obtained. This gas mixture was fed directly into reactor R2 at 220° C. In the first hour an average $CH_3Br$ conversion of 91% with an average dimethyl ether selectivity of 75% was obtained.

Summarizing the overall process in Reaction 2:

$$CH_3Br + HBr + CuO > CH_3OH + CuBr_2 \qquad (2)$$

Possible variations of Reaction 2:

$$2HBr + CuO > H_2O + CuBr_2 \qquad (2a)$$

$$2CH_3Br + CuO > CH_3OCH_3 + CuBr_2 \qquad (2b)$$

Reaction 3

The solid $CuBr_2/ZrO_2$ was transferred from Reactor 2 to Reactor 3 and treated with $O_2$ at 300° C. to yield $Br_2$ and $CuO/ZrO_2$ at 100% yield and conversion. This reaction may be run at 1000 $h^{-1}$.

Summarizing the overall process in Reaction 3:

$$CuBr_2/ZrO_2 + \tfrac{1}{2}O_2 > Br_2 + CuO/ZrO_2 \qquad (3)$$

Overall $$CH_4 + \tfrac{1}{2}O_2 > CH_3OH \qquad (A)$$

Possible variation $$CH_4 + \tfrac{1}{2}O_2 > \tfrac{1}{2}CH_3OCH_3 + 1/2H_2O \qquad (B)$$

A third embodiment of the invention comprises a process for converting ethane to diethyl ether, ethanol, and ethyl acetate which may be carried out as illustrated in FIGS. 1, 2, and 3. In the process, ethane reacts with bromine to form bromoethane and HBr. The bromoethane then reacts with metal oxide to form diethyl ether, ethanol, ethyl acetate, and metal bromide. The metal bromide reacts with oxygen or air to regenerate the original metal oxide. In the process, bromine and metal oxide are recycled.

It is well known that ethane can easily react with bromine at low temperatures (below 400° C.) to form bromoethane or ethane dibromides. If a suitable catalyst is used, the selectivity to ethane monobromide or dibromides is high. The reaction is slightly exothermal and is very easy to control. In the next reaction, bromoethane is converted to diethyl ether with 60 to 80% conversion and selectivity over 80% with about 4% selectivity to ethanol and about 3% selectivity to ethyl acetate. Hence, high diethyl ether yield with useful ethanol and ethyl acetate by products is obtained in a single pass. In the process, there is no direct contact between oxygen and ethane thereby providing a high level of safety. If desired, the diethyl ether can be easily hydrolyzed to ethanol with water over a suitable catalyst.

EXAMPLE

Part A. Ethane Bromination Reaction

A mixture of ethane (6.0 ml/minute) and bromine ($Br_2$ 0.30 ml/hour) was passed into a reactor (glass tube, ID 0.38", heating zone length 4"), and was heated to 330° C. The effluent was analyzed by GC/MS. 100% bromine conversion with 80% bromoethane selectivity was obtained. The by product with 20% selectivity was 1,1-dibromoethane. The 1,1-dibromoethane can be converted to bromoethane by reaction with ethane over a catalyst, such as a metal compound or a mixture of metal compounds.

The ethane bromination reaction can also be a catalysis reaction. The catalysts are compounds of Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B, Al, Ga, In, Tl, Si, Ge, Sn, Pb, P, Sb, Bi, S, Cl, Br, F, Sc, Y, Mg, Ca, Sr, Ba, Na, Li, K, O, La, Ce, Pr, Nd, Sm, Eu, Gd, Tb, Er, Yb, Lu, and Cs or mixtures thereof. The reaction is preferably carried out at a temperature range of between about 50° C. to about 600° C. The reaction pressure is preferably from about 1 to about 200 atm. The reaction mixture can have a ratio of ethane to bromine from 0.1 to 100.

Part B. Reaction of Bromoethane With Metal Oxides

Zr Solution Metal Oxide Preparation $Zr(OCH_2CH_2CH_3)_4$ (70(w) % in isopropanol, 112.6 ml) was dissolved into acetic acid (275 ml) under stirring. After stirring for 10 minutes, the solution was diluted with water to make a total volume of 500 ml. A solution with a Zr concentration of 0.5M was obtained.

Preparation of M4

A $Cu(NO_3)_2$ (0.5M, 64.0 ml) solution was added into a Zr solution (0.5M, 64.0 ml) (as prepared above). After stirring for a few seconds, a gel was obtained. The gel was dried at 110° C. for 4 hours, then heated to 500° C. within 6 hours, and calcined at 500° C. for 4 hours. $CuO/ZrO_2$ metal oxide (M4) was obtained.

Testing

Bromoethane (0.20 ml/hour) and helium (4.0 ml/minute) were passed through a reactor that was packed with 3.0000 grams M4, which was heated to 200° C. Within the first hour, an average bromoethane conversion of 70%, with diethyl ether 84 to 90% selectivity was obtained. The ethanol selectivity was about 4% and, ethyl acetate selectivity was about 3%.

In the above reaction, the metal oxides can be oxides of the following metals: Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B, Al, Ga, In, Tl, Si, Ge, Sn, Pb, P, Sb, Bi, S, Cl, Br, F, Sc, Y, Mg, Ca, Sr, Ba, Na, Li, K, La, Ce, Pr, Nd, Sm, Eu, Gd, Tb, Er, Yb, Lu, and Cs or mixtures thereof.

The reaction can be carried out at a temperature range from about 50° C. to about 600° C. The reaction pressure is preferably from about 1 to about 200 atm. The reaction can be carried out with or without helium. The metal bromide is converted to metal oxide M4 in oxygen or air to obtain metal oxide and bromine at a temperature range of about 50 to about 700° C. and pressure range from about 1 to about 300 atm.

A fourth embodiment of the invention comprises a process for converting saturated hydrocarbons (alkanes) to their corresponding olefins. For instance, ethane to ethylene, propane to propylene, butane to butene or butadiene, isobutane to isobutene, etc. The process of the third embodiment may be carried out as illustrated in FIG. 3.

In the process, alkane reacts with $CBr_4$, $CHBr_3$, or $CH_2Br_2$, or reacts with bromine to form brominated alkanes and HBr. The brominated alkane then reacts with metal oxide to form olefin and metal bromide. The metal bromide reacts with oxygen or air to regenerate the metal oxide. In the process, bromine and metal oxide are recycled.

In the prior art, olefins are made by hydrocarbon thermal cracking. The thermal cracking process also produces saturated hydrocarbons, such as propane, butane, isobutane, pentanes, and hexanes, which are usually difficult to convert to useful materials. For example, ethane can be converted to ethylene by thermal cracking at temperatures over 800° C. in an endothermic reaction, which consumes large amounts of energy, and also generates about 30% by product acetylene ($C_2H_2$). The acetylene must be hydrogenated back to ethylene which usually leads to over hydrogenation to ethane.

Propane is currently used as fuel, since there presently exists no efficient process that can convert propane to propylene.

There has been research directed at oxidizing alkanes to their corresponding olefins by reacting the alkane with oxygen over catalysts. However, low selectivity and low conversion rates were obtained. The reaction generates large amounts of heat, which can melt the catalyst as well as the reactor. Further, most of these processes involve the direct contact of the alkane with oxygen at high temperature and pressure, which is potentially dangerous.

It is well known that alkanes can easily react with $CBr_4$, $CHBr_3$, or $CH_2Br_2$, or react with bromine at low temperatures (below 400° C.) to form alkane monobromides or alkane dibromides. If a suitable catalyst is used, the selectivity to alkane monobromide or dibromide can be very high (more than 95% $CH_3CH_2BrCH_3$ selectivity can be reached). The reaction is slightly exothermal and is very easy to control. In the next reaction, alkane bromide is converted to olefin with 100% conversion (one pass) and selectivity over 95%. Hence, high olefin yield can be obtained in a single pass. In the process, the direct contact of oxygen with alkane is avoided, making the operation safe. A further advantage of the present invention is the virtual elimination of byproducts, rendering recovery of the desired olefin substantially easier than in conventional processes. An even further advantage of the present invention is the production of the olefin without the production of the corresponding alkyne, thus eliminating the need for partial hydrogenation.

EXAMPLE

Part A. Alkane Bromination Reaction

Propane Bromination Reaction

A mixture of propane (6.0 ml/minute) and bromine ($Br_2$ 0.30 ml/hour) was passed into a reactor (glass tube ID 0.38", heating zone length 4"), which was heated to 270° C. The effluent was analyzed by GC/MS. 100% bromine conversion with 88.9% 2-bromopropane selectivity and 11.1% 1-bromopropane selectivity were obtained.

This reaction can also be a catalysis reaction. The catalysts are compounds of Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B, Al, Ga, In, Tl, Si, Ge, Sn, Pb, P, Sb, Bi, S, Cl, Br, F, Sc, Y, Mg, Ca, Sr, Ba, Na, Li, K, O, La, Ce, Pr, Nd, Sm, Eu, Gd, Tb, Er, Yb, Lu, and Cs or mixtures of such compounds. The reaction can be carried out at a temperature range from about −10° C. to about 600° C. The reaction pressure can be from about 1 to about 200 atm. The reaction mixture can have a ratio of propane to bromine from 0.1 to 100.

Bromination of Isobutane

A mixture of isobutane (6.0 ml/minute) and bromine ($Br_2$ 0.30 ml/hour) was passed into a reactor (glass tube ID 0.38", heating zone length 4"), which was heated to 220° C. The effluent was analyzed by GC/MS. 100% bromine conversion with 99% 2-bromo-2-methyl-propane selectivity was obtained.

This reaction can also be a catalysis reaction. The catalysts are compounds of Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B, Al, Ga, In, Tl, Si, Ge, Sn, Pb, P, Sb, Bi, S, Cl, Br, F, Sc, Y, Mg, Ca, Sr, Ba, Na, Li, K, O, La, Ce, Pr, Nd, Sm, Eu, Gd, Tb, Er, Yb, Lu, and Cs or mixtures of such compounds. The reaction can be carried out at a temperature range from about −10° C. to about 600° C. The reaction pressure can be from about 1 to about 200 atm. The reaction mixture can have a ratio of isobutane to bromine from 0.1 to 100.

Part B. Reaction of Alkane Bromides With Metal Oxides

Preparation of Zr Solution $Zr(OCH_2CH_2CH_3)_4$ (70(w) % in isopropanol, 112.6 ml) was dissolved into acetic acid (275 ml) under stirring. After stirring for 10 minutes, the solution was diluted with water to make a total volume of 500 ml. A solution with a Zr a concentration of 0.5M was obtained.

Preparation of M5

A $Cu(NO_3)_2$ (0.5M, 4.00 ml) solution was added into $CaBr_2$ (0.5M, 4.00 ml). A clear solution was obtained. To this solution, Zr solution (0.5M, 8.0 ml) as prepared above was added under stirring. After stirring for a few seconds, a gel was obtained. The gel was dried at 110° C. for 4 hours, then heated to 500° C. within 6 hours, and calcined at 500° C. for 4 hours. M5 was obtained.

Preparation of M6

A $Cu(NO_3)_2$ (0.5M, 7.20 ml) solution was added into $BaBr_2$ (0.5M, 0.80 ml). A clear solution was obtained. To this solution, Zr solution (0.5M, 8.0 ml) as prepared above was added under stirring. After stirring for a few seconds, a gel was obtained. The gel was dried at 110° C. for 4 hours, then heated to 500° C. within 6 hours, and calcined at 500° C. for 4 hours. M6 was obtained.

Preparation of M7

A $Cu(NO_3)_2$ (0.5M, 8.00 ml) solution was added into Zr solution (0.5M, 8.0 ml) as prepared above was added under stirring. After stirring for a few seconds, a gel was obtained. The gel was dried at 110° C. for 4 hours, then heated to 500° C. within 6 hours, and calcined at 500° C. for 4 hours. M7 was obtained.

Testing on M5

2-bromopropane (0.25 ml/hour) and nitrogen (5.0 ml/minute) were passed through a reactor (glass tube ID 0.38", heating zone length 4") that was packed with 0.8701 gram M5 and heated to 200° C. 100% 2-bromopropane conversion with more than 95% propylene selectivity was obtained within the first 40 minutes. As the reaction proceeds the CuO is converted to $CuBr_2$ and the 2-bromopropane conversion rate decreases. When the reaction was carried out at 180° C., within the beginning 10 minutes, 99% propylene selectivity was reached with 2-bromopropane conversion more the 60%.

1-bromo-2-methyl-propane (0.29 ml/hour) and nitrogen (5.0 ml/minute) were passed through a reactor (glass tube ID 0.38", heating zone length 4") that was packed with 0.8701 gram M5 and heated to 220° C. 100% 1-bromo-2-methyl-propane conversion with more than 96% 2-methylpropylene selectivity was obtained within the first hour. As the reaction progresses and the CuO is converted to $CuBr_2$ the 2-bromopropane conversion decreases.

1-bromo-propane (0.24 ml/hour) and nitrogen (5.0 ml/minute) were passed through a reactor (glass tube ID 0.38", heating zone length 4") that was packed with 0.8701 gram M5 and heated to 220° C. 100% 1-bromo-propane conversion with more than 90% propylene selectivity was obtained within the first 20 minutes.

2-bromo-2-methyl-propane (0.31 ml/hour) and nitrogen (5.0 ml/minute) were passed through a reactor (glass tube ID 0.38", heating zone length 4") that was packed with 0.8701 gram M5 and heated to 180° C. 100% 2-bromo-2methyl-propane conversion with more than 96% 2-methylpropylene selectivity was obtained within the first hour.

Testing on M6

A mixture of 1-bromopropane and 2-bromopropane (volume 1:1) (0.25 ml/hour) and nitrogen (5.0 ml/minute) was passed through a reactor (glass tube ID 0.38", heating zone length 4") that was packed with 0.8980 gram M6 and heated to 200° C. 100% reactant conversion with more than 90% propylene selectivity was obtained within the first 10 minutes.

Testing on M7

A mixture of 1-bromo-2-methyl-propane and 2-bromo-2-methyl-propane (volume 1:1) (0.30 ml/hour) and nitrogen (5.0 ml/minute) were passed through a reactor (glass tube ID 0.38", heating zone length 4") that was packed with 0.8500 gram M7 and heated to 220° C. 100% reactant conversion with more than 95% propylene selectivity was obtained within the first 40 minutes.

The metal oxides used above can be oxides of the following metals: Ti, Zr, Hf, V, Nb, Ta, Cr, Mo, W, Mn, Re, Fe, Ru, Co, Rh, Ir, Ni, Pd, Pt, Cu, Ag, Au, Zn, Cd, B, Al, Ga, In, Tl, Si, Ge, Sn, Pb, P, Sb, Bi, S, Cl, Br, F, Sc, Y, Mg, Ca, Sr, Ba, Na, Li, K, La, Ce, Pr, Nd, Sm, Eu, Gd, Tb, Er, Yb, Lu, and Cs and mixtures thereof. The reaction can be carried out at a temperature range from about 50° C. to about 600° C. The reaction pressure can be from about 1 to about 200 atm. The reaction can be carried out with or without nitrogen. The metal bromide was converted to metal oxide (M5, M6, and M7) in oxygen or in air to obtain metal oxide and bromine at a temperature range of about 50 to about 700° C. under pressure range from about 1 to about 300 atm.

It will therefore be understood that the method and apparatus of the present invention operates on a continuous or batch basis to convert alkanes to alcohols, ethers, and olefins. The method and apparatus of the present invention operates at relatively low temperatures and at low pressures and is therefore economical to manufacture and use. The bromine, which is utilized in the method and apparatus of the present invention, is continuously recycled. The metal oxide, which is utilized in the process is continuously refreshed.

Although preferred embodiments of the invention have been illustrated in the accompanying Drawings and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method for synthesizing diethyl ether, ethanol, and ethyl acetate from ethane comprising:
   providing a quantity of ethane;
   providing a quantity of bromine;
   mixing the ethane with the bromine and thereby forming bromoethane and hydrogen bromide;
   directing the bromoethane into engagement with a metal oxide and thereby forming diethyl ether, ethanol, ethyl acetate, and a metal bromide;
   converting the metal bromide to form the original metal oxide and bromine;
   recycling the metal oxide; and
   recycling the bromine.

2. The method according to claim 1 wherein the step of mixing the ethane and the bromine is carried out at an ethane to bromine ratio from about 1:10 to 100:1 (mol).

3. The method according to claim 1 wherein the step of mixing the alkane and the bromine is carried out at a temperature of between about 50° C. and about 600° C.

4. The method according to claim 1 wherein the step of mixing the alkane and the bromine is carried out at a pressure between 0.1 to 200 atm.

5. The process according to claim 1 wherein the step of reacting the ethane with the bromine to form the bromoethane and the step of contacting the bromoethane with metal oxide are carried out continuously.

6. The process according to claim 1 wherein the step of reacting the ethane with the bromine to form the bromoethane and the step of contacting the bromoethane with metal oxide are carried out in a batch reaction.

7. The method according to claim 1 wherein the step of converting the metal bromide to form the original metal oxide and bromine, the step of recycling the metal oxide, and the step of recycling the bromine are carried out continuously.

8. The method according to claim 1 wherein the step of converting the metal bromide to form the original metal oxide and bromine, the step of recycling the metal oxide, and the step of recycling the bromine are carried out in a batch reaction.

9. An apparatus for converting ethane to diethyl ether, ethanol, and ethyl acetate comprising:
   a reactor;
   means for directing ethane and bromine into the reactor to produce bromoethane and hydrogen bromide;
   a first metal oxide bed comprising a solid metal oxide in a housing;
   means for directing the bromoethane and the hydrogen bromide into the first metal oxide bed such that hydrogen bromide is converted to water and metal bromide;
   means for separating the water from the bromoethane;
   a second metal oxide bed comprising a solid metal oxide in a housing;
   means for directing the bromoethane into the second metal oxide bed to form diethyl ether, ethanol, ethyl acetate, and the metal bromide;
   means for converting the metal bromide to form the original metal oxide and bromine; and
   means for recycling the original metal oxide and the bromine.

10. A method for converting ethane to diethyl ether comprising:
    providing a quantity of ethane;
    providing a quantity of bromine;
    reacting the ethane with the bromine and thereby forming bromoethane and hydrogen bromide;
    directing the bromoethane into engagement with a metal oxide and thereby forming diethyl ether and a metal bromide;
    converting the metal bromide to form the original metal oxide and bromine;
    recycling the metal oxide; and
    recycling the bromine.

11. The method according to claim 10 wherein the step of mixing the ethane and the bromine is carried out at an ethane to bromine ratio from about 1:10 to about 100:1 (by mole).

12. The method according to claim 10 wherein the step of mixing the ethane and the bromine is carried out at a temperature of between about 50° C. and about 600° C.

13. The method according to claim 10 wherein the step of mixing the ethane and the bromine is carried out at a pressure of between 0.1 to 200 atm.

14. The process according to claim 10 wherein the step of mixing the ethane and the bromine to form the bromoethane and hydrogen bromide and the step of contacting the bromoethane with a metal oxide are carried out continuously.

15. The process according to claim 10 wherein the step of mixing the ethane and the bromine to form the bromoethane and hydrogen bromide and the step of contacting the bromoethane with a metal oxide are carried out in a batch reaction.

16. The method according to claim 10 wherein the step of converting the metal bromide to form the original metal oxide catalyst and bromine, the step of recycling the metal oxide, and the step of recycling the bromine are carried out continuously.

17. The method according to claim 10 wherein the step of converting the metal bromide to form the original metal oxide catalyst and bromine, the step of recycling the metal oxide, and the step of recycling the bromine are carried out in a batch reaction.

18. The method of claim 10 wherein the step of engaging the bromoethane with the metal oxide also produces ethanol.

* * * * *